US012648702B1

(12) United States Patent

Chase

(10) Patent No.: US 12,648,702 B1

(45) Date of Patent: Jun. 9, 2026

(54) BLEEDING NAVIGATION DEVICE

(71) Applicant: William Chase, Avon, CT (US)

(72) Inventor: William Chase, Avon, CT (US)

( * ) Notice: Subject to any disclaimer, the term of this patent is extended or adjusted under 35 U.S.C. 154(b) by 0 days.

(21) Appl. No.: 19/063,457

(22) Filed: Feb. 26, 2025

(51) Int. Cl.
*A61B 5/00* (2006.01)
*A61B 5/02* (2006.01)

(52) U.S. Cl.
CPC ........ *A61B 5/02042* (2013.01); *A61B 5/0084* (2013.01)

(58) Field of Classification Search
CPC .................................................. A61B 5/02042
See application file for complete search history.

(56) References Cited

U.S. PATENT DOCUMENTS

| 2012/0022562 A1* | 1/2012 | Willard .............. A61B 17/0057 |
| | | 600/407 |
| 2020/0367720 A1* | 11/2020 | Zhao .................. A61B 1/00045 |

* cited by examiner

*Primary Examiner* — Joseph M Santos Rodriguez
(74) *Attorney, Agent, or Firm* — McCormick, Paulding & Huber PLLC

(57) ABSTRACT

A wound navigation device and method of evaluating a bleeding wound including the step of inserting the bleeding navigation device into a bleeding wound of an animal. The wound navigation device the bleeding navigation device includes a body, at least one light source arranged on and/or within the body, at least one optoelectronic sensor arranged on and/or within the body, and a processor operatively connected to the at least one light source and configured to receive detection data from the at least one optoelectronic sensor. Light is emitted from the at least one light source while the body is inserted into the bleeding wound. The at least one optoelectronic sensor detects reflected light while the body is inserted into the bleeding wound in order to determine direction of active bleeding source(s).

18 Claims, 2 Drawing Sheets

BLEEDING NAVIGATION DEVICE

TECHNICAL FIELD

The present disclosure generally relates to apparatuses and methods for evaluating bleeding wounds.

BACKGROUND

When a person is suffering from a bleeding wound, it can sometimes be difficult to ascertain the particular source(s) of bleeding. Deep penetrating wounds, such as gunshot and stab wounds, can be difficult to navigate and identify the actively bleeding blood vessels. Excess time taken for navigating and identifying bleeding sources of a wound can lead to negative patient outcomes.

SUMMARY

In embodiments according to the present disclosure a bleeding navigation device includes a body, at least one light source arranged on and/or within the body, at least one optoelectronic sensor arranged on and/or within the body, and a processor operatively connected to the at least one light source and configured to receive detection data from the at least one optoelectronic sensor. The processor is configured to determine one or more directions or one or more magnitudes of bleeding of one or more active bleeding sources within a wound based on the received detection data.

A method of evaluating a bleeding wound according to embodiments of the present disclosure includes inserting a bleeding wound navigation device into a bleeding wound of an animal or person. Emitting light from the at least one light source of the bleeding navigation device while the body is inserted into the bleeding wound and detecting reflected light with the at least one optoelectronic sensor while the body is inserted into the bleeding wound.

Objects, features and advantages of the present invention will become apparent in light of the description of embodiments and features thereof, as enhanced by the accompanying figures.

DETAILED DESCRIPTION

Figure 1:
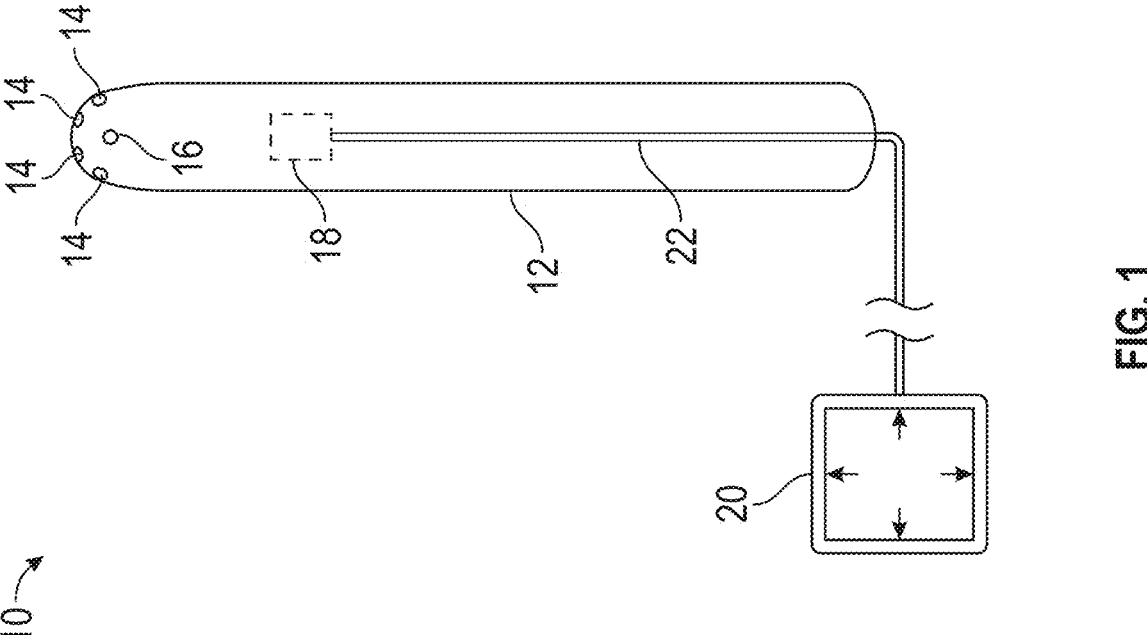
FIG. 1 is an illustration of a bleeding navigation device in accordance with the present disclosure.

Referring to FIG. 1, a bleeding wound navigation device 10 is shown according to the present disclosure. The device 10 includes a body 12 having a plurality of light sources 14 arranged on and/or within the body 12 and at least one optoelectronic sensor 16. The device 10 further includes a processor 18 operatively connected to the light source(s) 14 and arranged to receive data from the optoelectronic sensor(s) 16. The processor 18 is configured to generate output data to a display 20 through a wired connector 22 and/or through wireless communication (e.g. Bluetooth, Wi-Fi, etc.).

The light source(s) 14 is configured to emit visual light alone, infrared light alone, and/or a combination of visual light and infrared light at different times or simultaneously.

The optoelectronic sensor(s) 16 is configured to function as a photosensitive receiver. In operation, the sensor(s) 16 collect light emitted from the light source(s) 14 and reflected back from the interior features of a wound of a human or other animal. The sensor(s) 16 are configured to detect visual light and/or infrared light, and/or whatever spectrum of light the light source(s) 14 arranged to emit.

Figure 2:
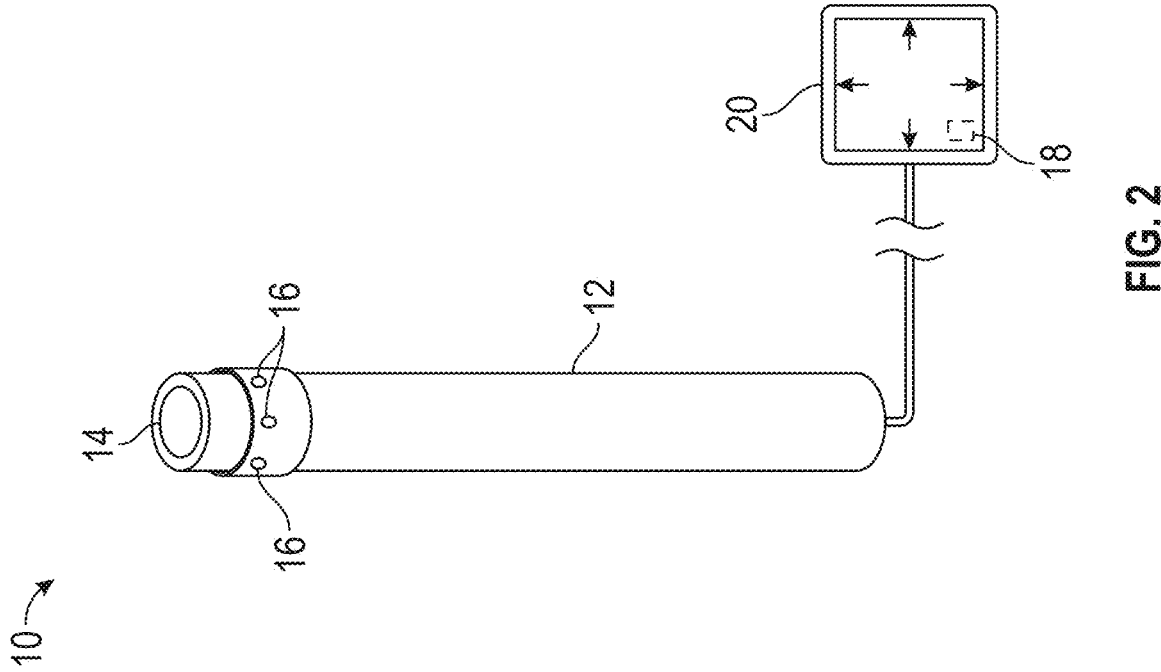
FIG. 2 is an illustration of a bleeding navigation device in accordance with the present disclosure.

The device 10 may comprise a single sensor 16 or an array of sensors 16 distributed circumferentially about the body 12 as shown in FIG. 2 of the drawings. In some embodiments, the body 10 is a rod.

Figure 3:
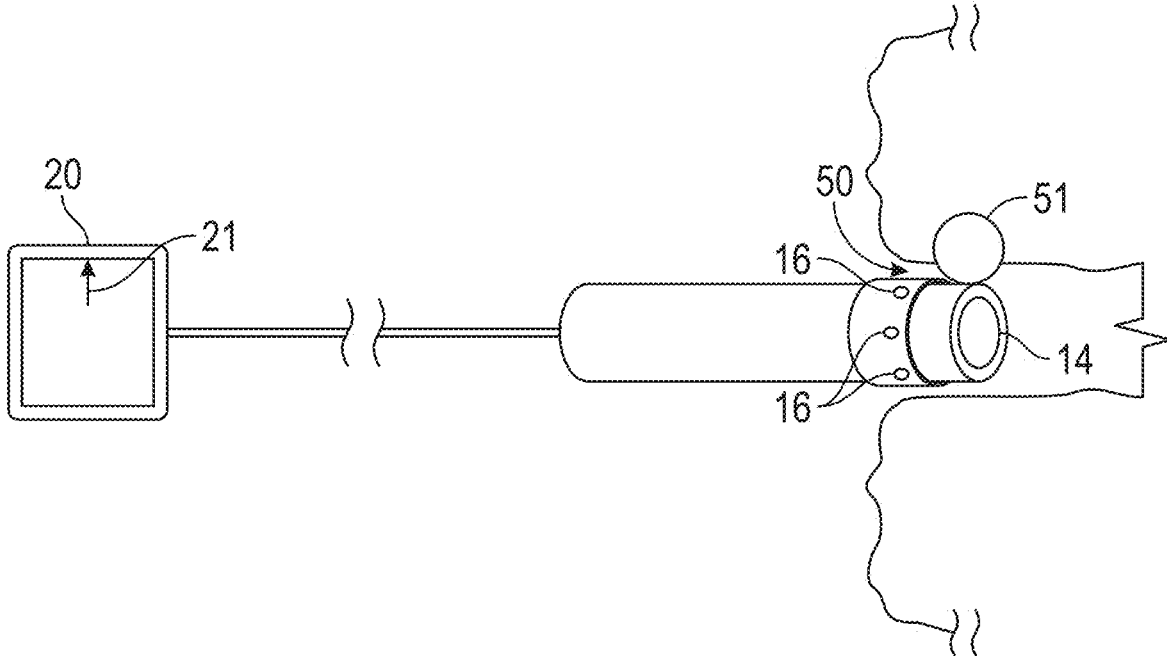
FIG. 3 is an illustration of a bleeding navigation device in use in a wound of a patient in accordance with the present disclosure.

In operation, the readings of the sensor(s) 16 are evaluated by the processor 18 to determine areas within a wound that have relative differences in blood concentration. The processor 18 is configured to generate an output signal that indicates the area(s) having higher blood concentration than other area(s) of the wound. For example, the processor 18 may generate an output signal that is provided to the display 20 for providing an indication of direction. In FIG. 3, the device 10 is shown inserted into a wound 50 with an active bleeding source 51 above the device 10. The device 10 detects this active bleeding source 51 and the processor 18 provides an output signal that causes an indication 21 being shown on the display 20. This advantageously provides an indication to a user of the device 10 of a directional source of bleeding, which allows for a more rapid assessment and treatment of the wound 50 of the patient.

While the processor 18 is shown as being arranged in the body 12, the processor 18 can be arranged elsewhere. For example, the processor 18 could be arranged in the display 20 or in another external enclosure that does not penetrate into the wound with the body 12. In some embodiments, the display 20 can be fixed to a proximal end of the body 12 (i.e. the opposite end of the body 12 that is inserted into the wound of the patient). In some embodiments, the display 20 is a simple arrangement of lights/indicators (e.g. arrows for indicating up, down, left, right, and/or diagonal directions therebetween) for indicating direction.

The technology and processes for using visual and infrared light to determine pulse rate and oxygen concentration of blood of an individual is well-known and documented. In some embodiments, instead of using a lookup table in an algorithm to convert measured returns into an absolute measurement, the relative values are used to identify areas of higher blood by way of differing levels of absorption.

In some embodiments, the processor 18 is configured to modulate the light emitted by the light source(s) 14. Modulated light emission allows for addition dimensions of readings.

In some embodiments, the device 10 is configured to modulate the light emitted by the light source(s) 14 by and obtain a reading from the different sensors. One light wavelength is emitted and measured then the light source 14 emits a second, different light wavelength and measured. The difference in measurements provides additional data. With a visual sensor, the light intensity can be adjustable, manually or automatically, in order to avoid overloading or interfering with the visual sensor(s).

In some embodiments, the device 10 is a standalone wound navigation/evaluation device. In some embodiments, the device 10 is integrated into an endoscope device that includes a traditional visual sensor for displaying images to an operator.

Although various features have been shown in different figures for simplicity, it should be readily apparent to one of skill in the art that various features may be combined without departing from the scope of the present disclosure.

The foregoing description of embodiments of the present invention has been presented for the purpose of illustration and description. It is not intended to be exhaustive or to limit the invention to the form disclosed. Obvious modifications and variations are possible in light of the above disclosure. The embodiments described were chosen to best illustrate the principles of the invention and practical applications thereof to enable one of ordinary skill in the art to utilize the invention in various embodiments and with various modifications as suited to the particular use contemplated.

What is claimed is:

1. A bleeding wound navigation device comprising:
a body;
at least one light source arranged on and/or within the body;
at least one optoelectronic sensor arranged on and/or within the body; and
a processor operatively connected to the at least one light source and configured to receive detection data from the at least one optoelectronic sensor;
wherein the processor is configured to determine one or more directions of one or more active bleeding sources within a wound based on the received detection data indicating areas in the wound having differing levels of absorption of light generated by the light source.

2. The bleeding wound navigation device according to claim 1, further comprising a display, wherein the processor is operatively connected to the display and configured to cause the display to generate an image based on detection data received from the at least one optoelectronic sensor.

3. The bleeding wound navigation device according to claim 2, wherein the processor is operatively connected to the display through a wired connection.

4. The bleeding wound navigation device according to claim 1, wherein the at least one light source is configured to emit light in the visual spectrum.

5. The bleeding wound navigation device according to claim 1, wherein the at least one light source is configured to emit light in the infrared spectrum.

6. The bleeding wound navigation device according to claim 1, wherein the at least one light source is configured to emit light in the visual spectrum and in the infrared spectrum.

7. The bleeding wound navigation device according to claim 1, wherein the at least one light source comprises a plurality of light sources.

8. The bleeding wound navigation device according to claim 1, wherein the at least one optoelectronic sensor comprises a plurality of optoelectronic sensors.

9. The bleeding wound navigation device according to claim 8, wherein the plurality of optoelectronic sensors are circumferentially arranged about the body.

10. The bleeding wound navigation device according to claim 8, wherein the plurality of optoelectronic sensors are configured to detect light through a 360° range of detection of the body.

11. The bleeding wound navigation device according to claim 1, wherein the processor is configured to generate an indication of a direction of a bleed source based on the detection data received from the at least one optoelectronic sensor.

12. The device according to claim 11, wherein the processor is configured to cause the indication of the direction of the bleed source to be generated on a display.

13. A method of evaluating a bleeding wound comprising:
inserting a bleeding wound navigation device into a bleeding wound of an animal, the bleeding wound navigation device comprising:
a body;
at least one light source arranged on and/or within the body;
at least one optoelectronic sensor arranged on and/or within the body; and
a processor operatively connected to the at least one light source and configured to receive detection data from the at least one optoelectronic sensor;
emitting light generated from the at least one light source of the bleeding navigation device while the body is inserted into the bleeding wound;
detecting reflected light with the at least one optoelectronic sensor while the body is inserted into the bleeding wound; and
determining, by the processor, one or more directions of bleeding within the bleeding wound based on the detection data indicating areas in the wound having differing levels of absorption of light generated by the at least one light source.

14. The method according to claim 13, wherein the animal is human.

15. The method according to claim 13, wherein the at least one light source comprises a plurality of light sources, and wherein the emitting light comprises emitting light from each of the plurality of light sources.

16. The method according to claim 13, wherein the at least one optoelectronic sensor comprises a plurality of optoelectronic sensors, and wherein the detecting reflected light comprises detecting reflected light with each of the plurality of optoelectronic sensors.

17. The method according to claim 13, further comprising generating, with the processor, an indication of a direction of a bleed source based on detection data received from the at least one optoelectronic sensor.

18. The method according to claim 17, further comprising displaying, with a display, the indication of the direction of the bleed source.

* * * * *